United States Patent
Hoehne

(10) Patent No.: US 10,968,115 B2
(45) Date of Patent: Apr. 6, 2021

(54) WATER DISINFECTION METHOD AND WATER TAPPING POINT ARRANGEMENT THEREFOR

(71) Applicant: Bernd Hoehne, Achim (DE)

(72) Inventor: Bernd Hoehne, Achim (DE)

(73) Assignee: Q One Holding AG, Sarnen (CH)

( * ) Notice: Subject to any disclaimer, the term of this patent is extended or adjusted under 35 U.S.C. 154(b) by 237 days.

(21) Appl. No.: 16/030,997

(22) Filed: Jul. 10, 2018

(65) Prior Publication Data
US 2019/0016610 A1    Jan. 17, 2019

(30) Foreign Application Priority Data

Jul. 13, 2017    (DE) .................. 10 2017 115 743.3

(51) Int. Cl.
*C02F 1/32* (2006.01)
*E03C 1/04* (2006.01)
(Continued)

(52) U.S. Cl.
CPC .............. *C02F 1/325* (2013.01); *A61L 2/10* (2013.01); *B05B 15/62* (2018.02); *E03C 1/04* (2013.01);
(Continued)

(58) Field of Classification Search
CPC ... B05B 15/62; B05B 1/18; E03C 1/04; E03C 1/0409; E03C 1/06; E03C 2201/40;
(Continued)

(56) References Cited

U.S. PATENT DOCUMENTS

| 5,891,329 A * | 4/1999 | Massholder ............ C02F 1/325 210/100 |
| 6,468,419 B1 | 10/2002 | Kunkel |
| 2016/0331855 A1 | 11/2016 | St. Louis et al. |

FOREIGN PATENT DOCUMENTS

| CN | 203695256 U | 7/2014 |
| CN | 103962256 A | 8/2014 |

(Continued)

OTHER PUBLICATIONS

CN-106216114-A Dec. 2016 Liu Jinlin Translation (Year: 2016).*
(Continued)

*Primary Examiner* — Cameron J Allen
(74) *Attorney, Agent, or Firm* — Patent Central LLC; Stephan A. Pendorf

(57) ABSTRACT

A method for disinfecting water by UV irradiation in water supply systems in buildings, ships or the like with a water tapping point connected flexibly to a hose (1), in particular hand shower (1'), and a water tapping point mount (2) for receiving (21) the water tapping point (1) when not in use, wherein the UV radiation takes place at the water tapping point (1). The UV-irradiation is directed from the water tapping point mount (2) to the water tapping point (1) when the water tapping point (1) is deposited in the water tapping point mount (2). Furthermore, the invention relates to a water tapping point. Means are provided for UV irradiation (3) of the water guided in the water tapping point (1). The means for UV irradiation (3) are arranged in the water tapping point mount (2), and a UV radiation transmissive window is provided in the water tapping point (1) opposite to the means for UV irradiation (3) when deposited (21) in the water tapping point mount (2).

20 Claims, 2 Drawing Sheets

Figure 1:
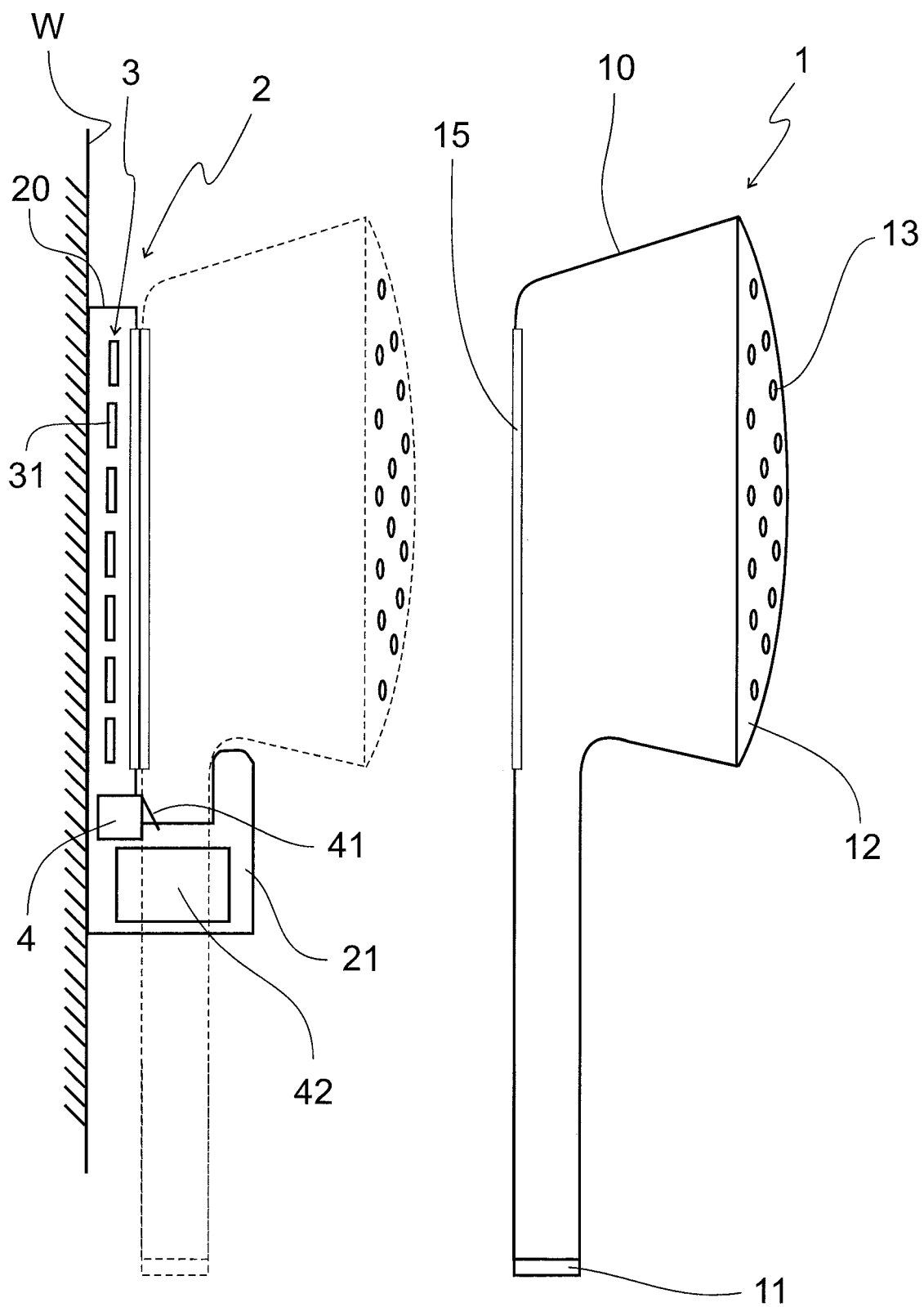

(51) Int. Cl.
*A61L 2/10* (2006.01)
*E03C 1/06* (2006.01)
*B05B 15/62* (2018.01)
*B05B 1/18* (2006.01)

(52) U.S. Cl.
CPC .............. *E03C 1/0409* (2013.01); *E03C 1/06* (2013.01); *B05B 1/18* (2013.01); *C02F 2201/3222* (2013.01); *C02F 2201/3227* (2013.01); *C02F 2307/06* (2013.01); *E03C 2201/40* (2013.01)

(58) Field of Classification Search
CPC .................. C02F 1/325; C02F 2307/06; C02F 2201/3222; C02F 2201/3227; C02F 1/32; A61L 2/10
See application file for complete search history.

(56) References Cited

FOREIGN PATENT DOCUMENTS

| | | |
|---|---|---|
| DE | 29614998 U1 | 11/1996 |
| DE | 19639802 A1 | 4/1998 |
| DE | 19736636 A1 | 2/1999 |
| DE | 10157355 A1 | 6/2002 |
| DE | 20105341 U1 | 8/2002 |
| GB | 2288974 A | 11/1995 |
| JP | 2001334179 A | 12/2001 |
| KR | 20080093535 A | 10/2008 |
| WO | 2011052986 A2 | 5/2011 |

OTHER PUBLICATIONS

International Search Report dated Aug. 31, 2018, in International Application No. PCT/DE2018/100463.
Office Action dated Jan. 22, 2018, in German Patent Application No. 10 2017 115 743.3.

* cited by examiner

WATER DISINFECTION METHOD AND WATER TAPPING POINT ARRANGEMENT THEREFOR

The invention relates to a method for the disinfection of water using UV-irradiation in water supply systems in buildings, ships or the like having a water tapping point connected flexibly to a hose, in particular a hand-held shower, and a water tapping point mount for holding the water tapping point when not in use, wherein the UV irradiation takes place at the water tapping point. Furthermore, the invention relates to a water tapping point arrangement in water supply systems in buildings, ships or the like with a water tapping point flexibly connected to a hose, in particular a hand-held shower, and a water tapping point mount for holding the water tapping point when not in use, where means are provided for UV irradiation of the water supplied in the water tapping point.

In water supply systems for industrial and drinking water in buildings and, for example, on ships it is known that germs, especially *Legionella*, multiply in them so that they are frequently identified as the cause of illnesses. Non-drying residual water in water tapping point in particular provides conditions that promote propagation the genus. The thusly contaminated water is then discharged in particular from shower heads in the form of from smallest drops to mist. This water mist can be easily inhaled and thus carries the risk of direct infection of the airways and lungs in humans Infection of lungs and respiratory tract with *Legionella* can lead to serious illnesses.

A commonly used countermeasure is to heat the entire piping system with high temperature water and then flush it with fresh water afterwards to rid the system of any germ residue. Other known countermeasures are central filtering of the water or central disinfection by means of chemical, electrical and also light technology methods, which are based on ultraviolet light (UV light).

The disadvantage of flushing with hot water is that the energy consumption and the water consumption are very high and the measure must be repeated regularly. Nevertheless, it is difficult to ensure that all the most vulnerable components are effectively disinfected.

The disadvantage of central filtration and disinfection systems is that even beneficial microbes and water components can thereby be reduced or destroyed. Since water in its original form with all ingredients is a natural consumable, a central disinfection is not in the interests of all consumers.

The disadvantage of all centrally functioning systems for the prevention of harmful germs, such as *Legionella*, is that they do not targetedly start at the points of the water supply system which have a special hazard potential, such as, in particular, taps and shower heads. Rather, the entire water supply must be disinfected in these central systems, resulting in a lot of effort and the particular vulnerability, namely taps and shower heads in particular, are nevertheless not sufficiently sanitized from unwanted microbial growth. In particular in the residual water at taps and especially in shower heads at room temperature and under the influence of air an accelerated *Legionella* growth can occur. Besides this, centralized systems cannot prevent genus from entering the system at non-central locations through possibly faulty components or other causes, spreading out, and then multiplying at sites that are favorable for them.

Therefore, systems for UV-irradiation in water tapping points, in particular shower heads, are known.

DE 101 57 355 A1 shows an embodiment in which the UV-irradiation is carried out in a feedwater supplying line immediately upstream of the shower head, for example in the shower hose. Thus disinfection by UV irradiation can be achieved on the line, however not of residual water remaining in the shower head.

A corresponding shower head is known from DE 196 39 802 A1, wherein after closing the tap water the remaining residual water in the shower head is irradiated by means of a UV-light and thus sterilized.

From DE 197 36 636 A1 a device for disinfecting water in a water tapping point by means of UV-irradiation is known in which first the UV-lamp is activated and only then is the water flow released from the water tapping point. This is a pre-sterilization to be achieved before the start of the water flow.

Similar arrangements are known from CN 203695256 U as well as JP 2001334179 A or KR 1020080093535 A.

Similarly, DE 201 05 341 U1 shows a device for disinfection and microbial sanitization of water and a shower or spray head with such a device. This is a flow-through device which has in the interior a hose of quartz glass, at which a lamp emitting ultraviolet light is provided. The water flows into two annular spaces and back again, wherein the two annular spaces are separated by another quartz glass hose in the flow path, so that the UV light can act on both flow paths.

Furthermore, US 2016/0331855 A1 discloses a disinfection system in which a UV light source is installed inside or outside a water tapping point with a transmission window or, as the case may be, the UV radiation is coupled directly into the water tapping point and thus into the water guided therein.

A disadvantage with these known UV-irradiation devices is that a disinfection with light can be achieved at the water tapping point only with irradiation elements housed directly there. This, in turn, brings about the requirement that the power supply is rendered electrically safe and is housed spatially in the housing of the showerhead and that all the elements for UV-irradiation are to be accommodated in the showerhead and must be carried by the user when using the hand-held shower. Only DE 101 57 355 A1 discloses coupling-in the UV-radiation in the area of the utility water connection via a connection piece in the flexible hose of the hand shower. In this embodiment, however, there is the disadvantage that a direct UV-irradiation on the shower head cannot be realized. Residual water present in the shower head can thus in turn serve as a breeding ground for the multiplication of genus, in particular *Legionella*.

The object of the invention is therefore to provide a method for the disinfection of water with a water tapping point flexibly connected to a hose or a corresponding water tapping point mount in which the water tapping point, in particular a hand shower, includes neither the UV-irradiation means nor the corresponding power supply, but nevertheless a UV radiation of the residual water present in the water tapping point may also take place.

This object is achieved with a method according to claim 1 and a water tapping point arrangement according to claim 6.

Since the UV radiation is directed from the water tapping point mount onto the water tapping point when the water tapping point is placed in the water tapping point mount, UV-irradiation is produced in the water tapping point mount and is directed on the water tap, so that UV-irradiation always takes place of the water tapping point when placed in the water tapping point mount and thus disinfection of the water contained in the water tapping point, including residual water, is possible.

According to the device aspect of the invention, this object is achieved in that the means for UV-irradiation are arranged in the water tapping point mount, and that a radiation window transparent to UV-irradiation is arranged in the water tapping point opposite to the means for UV irradiation. According to the invention, the water tap, in particular a hand-held shower, can be operated in a conventional manner, without the water tapping point being burdened with the weight and space requirement of additional electrical devices. All that is required is that a UV-radiation permeable window be provided at an appropriate location in the water tapping point, which can be irradiated by the corresponding UV-irradiation means in the water tapping point mount. Overall, it is ensured that by the UV-irradiation in the water tapping point directly in front of the water outlet a microbial growth is counteracted.

To ensure a disinfection of any residual water in the hose leading to the water tapping point, the UV radiation directed at the water tapping point is coupled from the water tapping point into the hose.

When the UV-irradiation is turned on and maintained for a predetermined duration after receiving the water tapping point in the water tapping point mount, the residual water remaining in tapping point after the use of the water tapping point is reliably UV-sterilized by the subsequent irradiation for a predetermined time.

Should a short time later the water tapping point be put back into operation, for example, in an interrupted shower or a second immediately following shower, to avoid unnecessary additional sterilization and thus to save energy, that the UV irradiation during a subsequent, renewed placement of the water tapping point in the water tapping point mount is only turned on when a predetermined first repeat interval is exceeded. For example, disinfection only needs to take place every 24 hours, 48 hours or even once a week. This can be adjusted depending on experience or testing.

On the other hand, it may be advantageous that the UV irradiation is turned on following non-use of the water tapping point, in the case that a predetermined second repetition interval is exceeded. For example, a UV-irradiation for sterilization of the remaining water should be repeated following a prolonged period of non-use, so that despite sterilization, after a prolonged period the microbe count is not too large. For example, such a disinfection can be repeated at least once a week or after a period of two or four weeks as the second repetition interval.

According to the device aspect of the invention, UVC-emitting LED semiconductors are preferred as a suitable means for UV irradiation, since they have a low power consumption in relation to their radiation intensity, quickly reach their desired radiation intensity and are easily adjustable to the optimum, germicidal wavelength of light.

If the means for ultraviolet irradiation are arranged waterproof in the water tapping point mount, in that a UV-light-permeable cover is provided on the water tapping point mount opposite to the UV-radiation transmissive window of the water tapping point, then also the UV-irradiation means housed in the water tapping point mount is protected from being affected by penetrating water. The UV-radiation is directed more or less through two UV-radiation permeable windows, one at the water tapping point mount and one in the water tapping point, to the residual water left in the water tapping point.

Thereby, that a light guide is provided in the hose, in which UV-radiation can be coupled from the water tapping point mount through the water tapping point to the hose, UV-radiation directed at the water tapping point from the water tapping point mount can be introduced into the hose via the light guide inserted therein. Thus, any residual water in the hose leading to the water tapping point can be disinfected.

In order to achieve the most uniform possible light distribution of the UV radiation in the hose, the light guide has a plurality of light emission points or a partial transparencies for the continuous light output of the UV radiation.

In a further embodiment the light guide has a length that is half or slightly greater than equal to the length of the hose. Thus, the light guide extends sufficiently far into the shower hose on the downstream side. Preferably, the light guide extends even to the shower control, so that residual water over the entire range of the hose and at the outlet opening of the shower control is disinfected by the UV-light supplied via the light guide. Any *Legionella* etc. in the residual water are thus killed and cannot multiply, even in this optimal environment for propagation.

It is further of advantage when the means for UV irradiation is supplied with power from a low voltage supply, or a battery is provided on the water tapping point mount, whereby the power supply is provided entirely on the water tapping point mount, which is fixedly arranged on the wall of the shower or bath. For retrofitting this arrangement, it is particularly preferred here if the means for UV-irradiation is provided with a battery in the water tapping point mount, thereby there is no additional installation work for laying a low voltage line in the area for water tapping point mount. In this case, it has been proven in laboratory tests that a supply of the UV-irradiation means in the water tapping point mount with a commercially available 9 V battery is sufficient for about 3,000 disinfections. Therewith, such a device with battery supply could be sufficient for at least two years in a normal use in a private bathroom. With both the power supply with a 9 V block battery as well as with supplied with low voltage it is ensured that the operator is protected at the water tapping point mount against any hazardous electrical shock.

In that an actuating means is provided at the water tapping point mount, which actuates the means for UV irradiation when the water tapping point on the water tapping point mount has not been used, preferably the UV-radiation when reactivation of the water tapping point, in particular a hand shower, is triggered in the water tapping point mount. If necessary, it can be provided that the UV-radiation begins only after a waiting period of for example 10 minutes, so that the user is not irritated or even compromised through the switched-on UV-irradiation.

Alternatively to the above-mentioned configuration, the water tapping point can be a hand shower with shower nozzles, wherein shading means are provided in the hand shower before the shower nozzles, whereby an unintended leakage of UV-light can be avoided. This shading ensures namely that no potentially harmful UVC radiation can escape from the shower nozzles in the shower head when showering or after using the shower head. The shading means prevents direct radiation contact from the UVC radiation source (LED semiconductor) to the skin or the eyes of the user.

Furthermore, it can be provided that in the control electronics for the means for UV irradiation, a safety circuit is provided, which terminates the UV irradiation immediately, as soon as a safety-relevant defect is detected. This may be, for example, a destruction of the housing of the water tapping point or the shower head or other technical defects that carry the risk that UVC radiation could escape unhindered from the component. As a safety switch, for example, light sensors, pressure sensors and/or humidity sensors are conceivable. Optionally, a signal communication between water tapping point and water tapping point mount is advantageous.

Hereinafter, a water tapping point arrangement invention will be described in detail with reference to the accompanying figures. It shows:

FIG. 1 a water tapping point arrangement in a side view and

Figure 2:
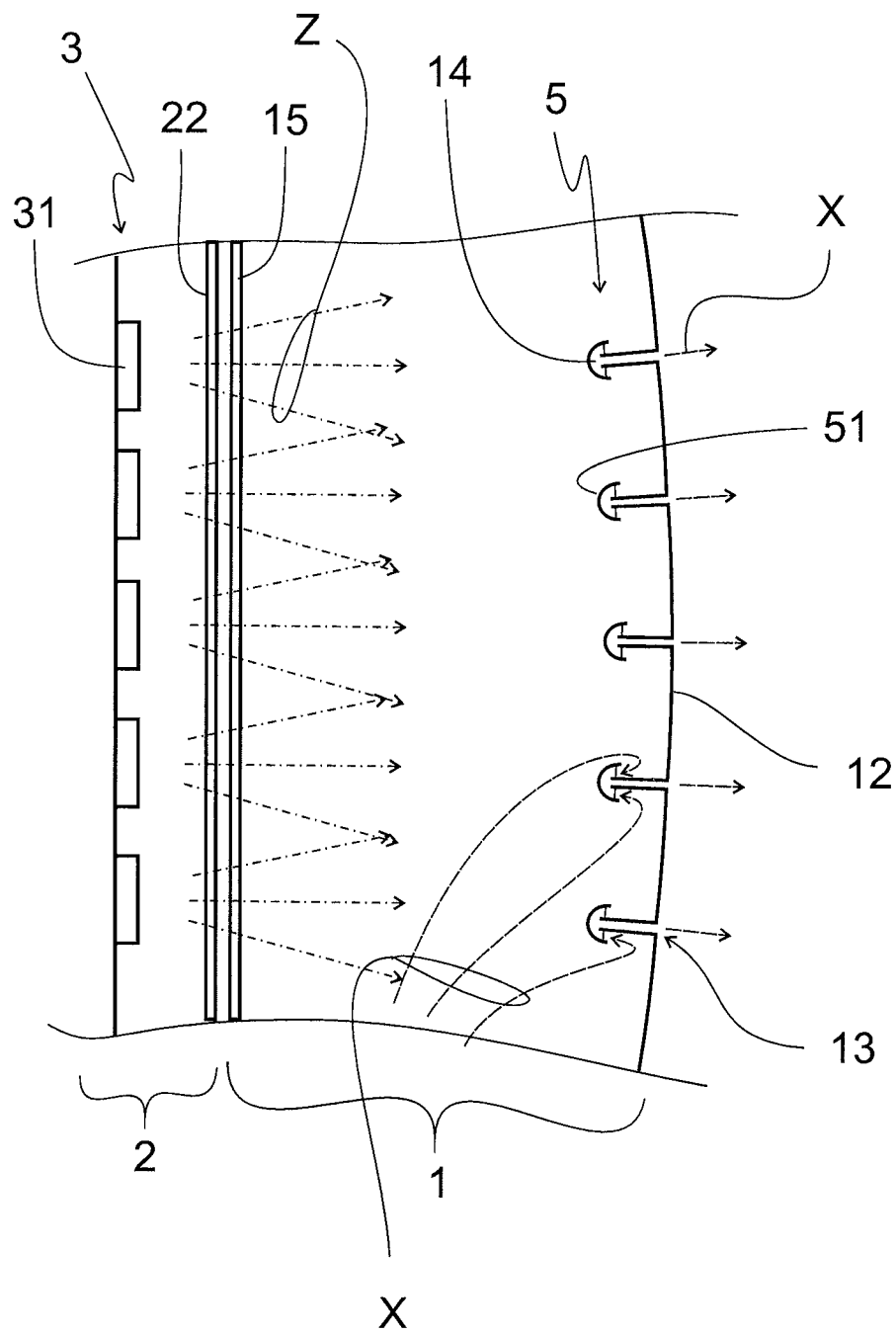

FIG. 2 in a detail view a part of the water tapping point.

FIG. 1 shows a water tapping point 1 in the form of a hand shower 1' and an associated water tapping point mount 2, which is attached to a wall W. The hand shower 1' can be stored in the water tapping point mount 2 in the manner shown in dashed line. Incidentally, the hand shower 1' is freely useable in the usual manner. The water tapping point 1, which is designed as a hand shower or shower head 1', is connected to a shower hose for water supply. At the downstream end of the shower head 1' a water outlet 12 with a plurality of shower nozzles 13 is fainted on the housing 10.

The water tapping point mount 2, which is fixed to the wall W, has a mount housing 20, on which a receptacle 21 for holding the shower head or the hand shower 1' is formed. Within the mount housing 20 of the water tapping point mount 2 a means for UV-irradiation 3 is arranged. The means for UV-irradiation 3 has a plurality of UVC emitting LEDs 31, which are for example provided on a circuit board. A requisite control electronics 4 can be are arranged on the board. In FIG. 1, the control electronics 4 shown as a box. At the control electronics 4, an actuating means 41 is arranged, which is actuated when hanging the hand shower 1' in the receptacle 21 of the water tapping point mount 2 and a signal "hand shower properly placed in the water tapping point mount 2" is reported. The power is supplied via a battery 42, which is also housed in the mount housing 20 of the water tapping point mount 2.

On the one hand to protect the electric components in the water tapping point mount 2 against moisture and at the same time to allow an emission of UV irradiation produced in the means of UV-radiation 3, a second UV-radiation transmissive window 22 is provided is in the mount housing 20. Likewise, a first window 15 transmissive for UV-radiation is arranged in the housing 10 of the hand shower 1', which during the intended placement of the hand-held shower in the water tapping point mount 2 accurately lies against the second UV-radiation transmissive window 22, so that the water tapping point mount 2 can act in the interior of the hand-held shower 1' by means of UV radiation generated in the means for UV-irradiation 3.

This situation is shown in FIG. 2 again in detail as a detail view, partially sectional. The UVC-irradiation Z emitted by the UVC emitting LED 31 of the means for UV-irradiation 3 act through the second UV-radiation transmissive window 22 and the parallel directly adjacent arranged first UV-radiation transmissive window 15 on the interior of the hand-held shower 1'. There any possible residual water is disinfected through the UVC-radiation.

In this case, the shower head or the hand shower 1' in another embodiment includes a shading 5 immediately before the shower nozzles 13. This situation is shown in FIG. 2 in a section in the shower head. The shading means 5 consists of a hood 51 which is arranged on the inside of the shower nozzle 13 in front of each flow inlet openings 14. This UVC-resistant and opaque hood 51 prevents UVC light from the LED semiconductors from being able to radiate through the shower nozzle 13 to the outside. The flow inlet 14 of the shower nozzle 13 is therefore safely protected against the penetration of UVC radiation Z through the hood 51. Since the hood 51 is arranged at a distance from the flow inlet 14 of the shower nozzle 13, the water to be dispensed from the shower head 1 can flow substantially unhindered through the shower nozzle 13 in accordance with the flow arrows X shown in FIG. 2.

The operation of the water disinfection process will be described below with reference to the water tapping point arrangement described herein.

If a user has used the hand shower 1' and then subsequently places the hand shower 1' into the water tapping point mount 2 in the designated receptacle 21, it is reported via the actuating means 41 of the control electronics 4, that a just used hand shower 1' has now been deposited. The control electronics 4 then activates the means for UV-irradiation by 3 to switch on the power supply from the battery 42 to the UVC emitting LED 31. Accordingly, the UV-irradiating of the interior of the hand-held shower 1' begins, since the UV-radiation, particularly preferably UVC-radiation Z, acts from the means of UV-irradiation 3 through the two windows 15, 22 into the interior space of the hand shower U.

Optionally, a predetermined waiting time, for example, 10 minutes, after hanging the hand shower 1' in the receptacle 21 of the water tapping point mount 2 can be preset, to avoid an impairment of the user by the UV-light. The waiting time is also specified, so that the disinfection program is not started anew every time, in order to allow for shower breaks, for example for soaping. What is important, in particular, is to disinfect for a long period of rest of the shower head. For this the control electronics 4 are provided a duty cycle according to predetermined minimum values to maintain a required adequate disinfection of the residual water in the hand shower P. By killing the germs remaining in the residual water (*Legionella*) it is prevented that the genus in the residual water could proliferate under the optimal propagation conditions prevailing there.

Furthermore, it can be achieved by providing a predetermined first repetition interval that water disinfection is not started again each time after using the hand shower. The first repetition interval may comprise, for example, 24 hours, 48 hours or even a whole week. This ensures that disinfection is only carried out once, for example, within 24 hours, regardless of the frequency of using the shower and placing the hand shower 1' in the water tapping point mount 2.

In addition, a second repetition interval may be programmed in the control electronics 4, which ensures that with a prolonged non-use of the shower any residual water located in the hand shower 1' with germs contained therein leads to further proliferation. This can be preset for example for a long period of inactivity, for example, two weeks or four weeks for the second repetition interval. This would mean that, for example, after four weeks of non-use of the hand shower 1' disinfection automatically proceeds.

LIST OF REFERENCE NUMBERS 1 water tapping point
1' shower head, hand shower
10 housing
11 inflow connection
12 water outlet
13 shower nozzle
14 flow inlet port
15 first window
2 water tapping point mount
20 mount housing 21 receptacle
22 second window
3 means for UV-radiation
31 UVC emitting LED
4 control electronics
41 actuating means
42 battery
5 shading
51 hood
W wall
X water flow direction
Z UVC-radiation

The invention claimed is:

1. A method for the disinfection of water by means of UV irradiation in water supply systems in buildings or ships having a water tapping point (1) flexibly connected to a hose, and a water tapping point mount (2) for receiving (21) the water tapping point (1) when not in use, where the UV radiation takes place at the water tapping point (1), the method comprising:
providing a means for UV-irradiation (3) in the water tapping point mount (2),
depositing the water tapping point (1) in the water tapping point mount (2) after use of the water tapping point (1),
directing UV-irradiation from the water tapping point mount (2) to the water tapping point (1) while the water tapping point (1) is received in the water tapping point mount (2).

2. The method according to claim 1, wherein UV-irradiation directed onto the water tapping point (1) is coupled from the water tapping point (1) into the hose.

3. The method according to claim 1, wherein after depositing (21) the water tapping point (1) in the water tapping point mount (2) the UV-irradiation is switched on and maintained for a predetermined duty cycle.

4. The method according to claim 3, wherein upon subsequent, renewed depositing (21') the water tapping point (1) in the water tapping point mount (2) the UV-irradiation is only switched on when a predetermined interval between the depositing (21) and the renewed depositing (21') is exceeded.

5. The method according to claim 4, wherein the predetermined interval between the depositing (21) and the renewed depositing (21') is 24 hours.

6. The method according to claim 4, wherein the predetermined interval between the depositing (21) and the renewed depositing (21') is 48 hours.

7. The method according to claim 4, wherein the predetermined interval between the depositing (21) and the renewed depositing (21') is one week.

8. The method according to claim 3, wherein in the case a predetermined time interval of non-use of the water tapping point (1) is exceeded the UV irradiation is turned on.

9. The method according to claim 8, wherein the predetermined time interval of non-use of the water tapping point (1) is one week.

10. The method according to claim 8, wherein the predetermined time interval of non-use of the water tapping point (1) is four weeks.

11. The method according to claim 1, wherein the water tapping point (1) is a hand shower (1').

12. A water tapping point arrangement in water supply systems in water supply systems in buildings or ships with a water tapping point (1) flexibly connected to a hose, and a water tapping point mount (2) for depositing (21) the water tapping point (1) when not in use,
wherein the water tapping point mount (2) includes a mount housing (20),
wherein means for UV irradiation (3) of the water guided in the water tapping point (1) is arranged in the water tapping point mount (2),
wherein a first window (15), transparent to UV radiation, is arranged in the water tapping point (1) opposite to the means for UV irradiation (3) when deposited (21) in the water tapping point mount (2),
wherein a second UV-radiation transmissive window (22) is provided in the mount housing (20) directly adjacent first UV-radiation transmissive window (15), and
wherein UV radiation emitted by the means for UV irradiation (3) acts through the second UV-radiation transmissive window (22) and the directly adjacent first UV-radiation transmissive window (15).

13. The water tapping point arrangement according to claim 12, wherein the means for UV irradiation (3) is UVC emitting LED semiconductors (31).

14. The water tapping point arrangement according to claim 12, wherein the means for UV irradiation (3) is provided watertight in the water tapping point mount (2) with a second UV-transparent window (22) in the water tapping point mount (2) opposite to the first, UV-radiation-transmitting window (15) of the water tapping point (1).

15. The water tapping point arrangement according to claim 12, wherein a light guide is provided in the hose, via which the UV radiation is coupled from the water tapping point mount (2) to the water tapping point (1).

16. The water tapping point arrangement according to claim 15, wherein the light guide has a plurality of light emission sites or a partial transparency for continuous light output for the UV radiation.

17. The water tapping point arrangement according to claim 15, wherein the light guide has a length which is ½ to greater than the length of the hose.

18. The water tapping point arrangement according to claim 12, wherein the means for UV irradiation (3) is provided with a power supply by means of supplied low voltage or battery (42) is provided at the water tapping point mount (2).

19. The water tapping point arrangement according to claim 12, wherein the water tapping point (1) is a hand shower with shower nozzles (13), wherein in the hand shower (1') a shading agent (5) is arranged in front of the shower nozzles (13).

20. A water tapping point arrangement in water supply systems in buildings or ships with a water tapping point (1) flexibly connected to a hose, and a water tapping point mount (2) for depositing (21) the water tapping point (1) when not in use,
wherein the water tapping point mount (2) includes a mount housing (20),
wherein means for UV irradiation (3) of the water guided in the water tapping point (1) is arranged in the water tapping point mount (2),
wherein a first window (15), transparent to UV radiation, is arranged in the water tapping point (1) opposite to the means for UV irradiation (3) when deposited (21) in the water tapping point mount (2),
wherein a second UV-radiation transmissive window (22) is provided in the mount housing (20) directly adjacent first UV-radiation transmissive window (15), and
wherein UV radiation emitted by the means for UV irradiation (3) acts through the second UV-radiation transmissive window (22) and the directly adjacent first UV-radiation transmissive window (15), wherein an actuating means (41) is provided at the water tapping point mount (2), which activates the means of UV irradiation (3) at the water tapping point mount (2) when the deposited (21) water tapping point (1) is not in use.

\* \* \* \* \*